United States Patent [19]

Clausen

[11] Patent Number: 4,942,224
[45] Date of Patent: Jul. 17, 1990

[54] A-ASSOCIATED H-ANTIGENS, MONOCLONAL ANTIBODIES SPECIFIC THERETO AND METHODS FOR EMPLOYING THE SAME IN BLOOD TYPING

[75] Inventor: Henrik Clausen, Seattle, Wash.

[73] Assignee: The Biomembrane Institute, Seattle, Wash.

[21] Appl. No.: 343,566

[22] Filed: Apr. 27, 1989

Related U.S. Application Data

[62] Division of Ser. No. 2,467, Jan. 12, 1987, Pat. No. 4,857,639.

[51] Int. Cl.$^5$ .................. C08B 37/00; C07H 1/00; C07H 3/00; A61K 37/00
[52] U.S. Cl. .................... 530/387; 530/395; 435/172.2; 435/240.26; 435/240.27; 935/103; 536/1.1
[58] Field of Search .................. 530/387, 395; 435/172.2, 240.26, 240.27; 935/103; 536/1.1

[56] References Cited

U.S. PATENT DOCUMENTS

| 4,029,762 | 6/1977 | Galanos et al. ............. 424/87 |
| 4,330,619 | 5/1982 | Goldstein ..................... 435/2 |
| 4,343,797 | 8/1982 | Ecanow ........................ 514/832 |
| 4,609,627 | 9/1986 | Goldstein ..................... 424/88 |
| 4,746,511 | 5/1988 | Kobatake et al. ............ 536/1.1 |
| 4,757,003 | 7/1988 | Matsumoto et al. .......... 435/7 |
| 4,762,824 | 8/1988 | Källenius et al. ............. 536/1.1 |

OTHER PUBLICATIONS

Race, R. R. et al., Blood Groups in Man, 6th Ed., pp. 9–13, Blackwell Scientific Publications, Oxford (1975).
Makela, O. et al., J. Immunol., 102:763–771 (1969).
Economidou, J. et al., Vox Sang., 12:321–328 (1967).
Mohn, J. F. et al., Human Blood Groups, pp. 316–325, Eds. Mohn, J. et al., Karger, Basel (1977).
Moreno, C. et al., J. Exp. Med., 134:439–457 (1971).
Kisailus, E. C. et al., J. Exp. Med., 147:830–843 (1978).
Clausen, H. et al., J. Biol. Chem., 261:1380–1387 (1986).
Clausen, H. et al., Proc. Natl. Acad. Sci., U.S.A., 82:1199–1203 (1985).
Hakomori, S., Semin. Hematol., 18:39–62 (1981).
Donald, A. S. R., Eur. J. Biochem., 120:243–249 (1981).
Kanagi, R. et al., J. Biol. Chem., 258: 8934–8942 (1983).
Kumazaki, T. et al., Proc. Natl. Acad. Sci. U.S.A., 81:4193–4197 (1984).
Graham, H. A. et al., Human Blood Groups: 5th International Convocation Immunology, Buffalo, N.Y. (1976), Eds. Mohn, J. F. et al., pp. 257–267, Karger, Bagel.
Kannagi, R. et al., FEBS Lett., 175: 397–401 (1984).
Clausen, H. et al., Biochem. Biophys. Res. Commun., 124:523–529 (1984).
Clausen, H. et al., J. Biol. Chem., 261:1388–1392 (1986).

Primary Examiner—Ronald W. Griffin
Attorney, Agent, or Firm—Sughrue, Mion, Zinn, Macpeak & Seas

[57] ABSTRACT

The present invention relates to antigens present in blood group A and blood group AB erythrocytes but absent in blood group B and blood group O erythrocytes. More specifically, the present invention relates to A-associated H-antigens having the following structure:

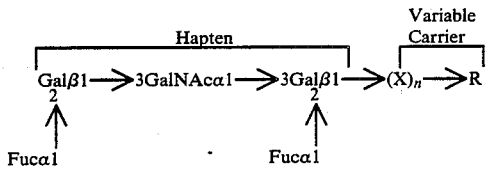

wherein X is a sugar residue and n=0 or a positive integer and wherein R is a primary amino group containing material selected from the group consisting of a polypeptide, a primary amino group containing lipid and a primary amino group containing support; monoclonal antibodies specific thereto and methods for employing the same in blood typing.

24 Claims, 4 Drawing Sheets

A-ASSOCIATED H-ANTIGENS, MONOCLONAL ANTIBODIES SPECIFIC THERETO AND METHODS FOR EMPLOYING THE SAME IN BLOOD TYPING

This is a division of application Ser. No. 07/002,467, filed Jan. 12, 1987, now U.S. Pat. No. 4,857,639.

FIELD OF THE INVENTION

The present invention relates to antigens present in blood group A and blood group AB erythrocytes but absent in blood group B and blood group O erythrocytes. More specifically, the present invention relates to A-associated H-antigens, monoclonal antibodies specific thereto and methods for employing the same in blood typing.

BACKGROUND OF THE INVENTION

Typing of blood is one of the most frequent and important laboratory techniques of medicine. Typing is based on a specific hemagglutination assay using erythrocytes from patients to be typed with human polyclonal antisera, i.e., anti-A and anti-B sera. Due to the variability and limited availability of human reagents, it has been of interest to develop standardized reagents which can be supplied in unlimited quantities. Recent developments in hybridoma antibody technology have enabled the development of various monoclonal antibodies with anti-A properties. However, these monoclonal anti-A antibodies generally fail to agglutinate the minor blood group A subgroups.

Blood group A has been subgrouped into the major subgroups $A_1$ and $A_2$ and minor subgroups $A_{3-5}$ and $A_x$ (see Race, R. R. et al, *Blood Groups in Man*, 6th Ed., pp. 9–13, Blackwell Scientific Publications, Oxford (1975)). The chemical difference between the two major phenotypes $A_1$ and $A_2$ has not been clarified, although several studies have indicated both quantitative (see Makela, O. et al, *J. Immunol.*, 102:763–771 (1969) and Economidou, J. et al, *Vox Sang.*, 12:321–328 (1967) and qualitative (see Economidou, J. et al, *Vox Sang.*, 12:321–328 (1967): Mohn, J. F. et al, *Human Blood Groups*, pp. 316–325, Eds. Mohn, J. et al, Karger, Basel (1977); Moreno, C. et al, *J. Exp. Med.*, 134:439–457 (1971) and Kisailus, E. C. et al, *J. Exp. Med.*, 147:830–843 (1978) differences in the expression of A antigen.

A large number of laboratories in the United States and other countries have attempted to develop monoclonal antibodies to cover minor $A_3$–$A_5$ and $A_x$ subgroups but to date, no satisfactory reagent has been produced.

SUMMARY OF THE INVENTION

An object of the present invention is to develop antigens which are associated with minor blood group A erythrocytes.

Another object of the present invention is to use these antigens to generate reagents, i.e., monoclonal antibodies with anti-A properties, useful for blood group A typing.

Still another object of the present invention is to provide a method of using the monoclonal antibodies for blood group A typing.

These and other objects of the present invention will be apparent from the detailed description of the invention below.

The above-described objects of the present invention have been met, in one embodiment, by A-associated H-antigens having the following structure:

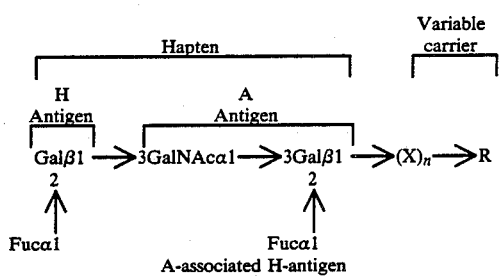

A-associated H-antigen wherein X is a sugar residue and n=0 or a positive integer and wherein R is a primary amino group containing material selected from the group consisting of a polypeptide, a primary amino group containing lipid and a primary amino group containing support; and monoclonal antibodies having binding specificity to the hapten of the A-associated H-antigen.

The hapten of the A-associated H-antigen is a combination of an H-antigen linked onto an A-antigen. The hapten of the A-associated H-antigen constitutes a unique antigenic entity associated specifically with minor A subgroups.

The hapten of the antigens of the present invention is present in blood group A and group AB erythrocytes but absent in blood group B and O erythrocytes.

The above-described objects have also been met, in a second embodiment, by monoclonal antibodies having binding specificity to A-associated H-antibodies.

The present invention is an improvement in the technology disclosed in Clausen, H. et al, *J. Biol. Chem.*, 261:1380–1387 (1986) which is incorporated by reference herein in its entirety.

DETAILED DESCRIPTION OF THE INVENTION

Figure 1A:
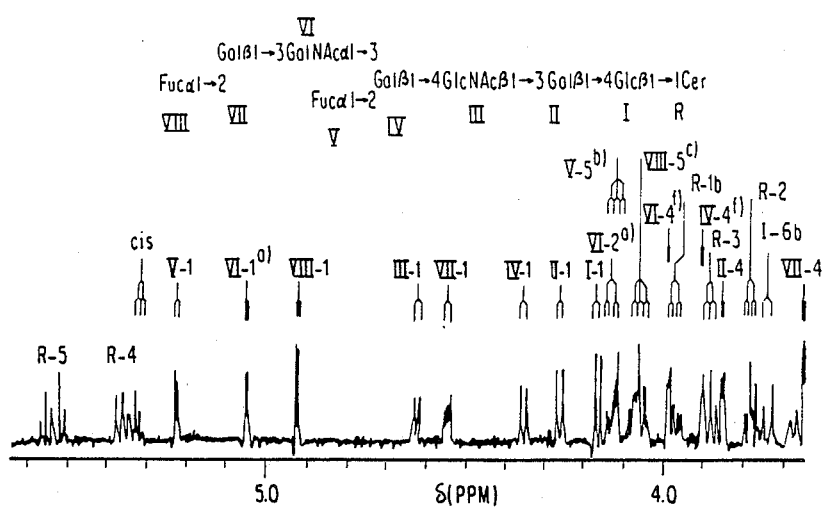
FIG. 1A is the downfield region of a resolution enhanced ($^1$H NMR) spectra, at 308°±2° K., of A-associated H-antigens obtained from A erythrocytes.

As discussed above, the objects of the present invention have been met, in one embodiment, by A-associated H-antigens having the following structure:

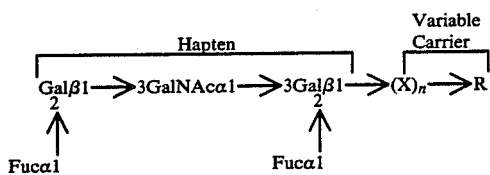

wherein X is a sugar residue and n=0 or a positive integer and wherein R is a primary amino group containing material selected from the group consisting of a polypeptide, a primary amino group containing lipid and a primary amino group containing support; and monoclonal antibodies having binding specificity to the hapten of the A-associated H-antigen.

As used herein, various abbreviations are defined as follows:

Fuc: L-fucose
Gal: D-galactose
GalNAc: D-N-acetylgalactosamine
GlcNAc: D-N-acetylglucosamine
Cer: ceramide
Ser: serine
Thr: threonine In the present invention, n is 0 or a positive integer. The specific length of the polysaccharide represented by $(X)_n$ is not critical to the present invention as long as the hapten of the A-associated H-antigen is accessible for antibody recognition. From an economic and practical standpoint n is no greater than about 30 and preferably n is 0 to 10. Where n is greater than 0, the sugar residues employed may be the same or different. Further, when n is greater than 0, the sugar chain may be branched or unbranched.

The particular sugar residues which can be employed in the present invention are not critical thereto. Examples of the sugar residues which can be employed in the present invention include a residue of β-D-galactose, β-D-glucose, β-D-N-acetylglucosamine, β-D-N-acetylgalactosamine, α-L fucose, α-D-galactose, α-D-acetylgalactosamine, α-D-mannose and β-D-mannose. The sugar residues can be those found in A-associated H-antigens isolated from A and AB erythrocytes or can be additional sugar residues which are added to the hapten of the A-associated H-antigen by well known means using well known enzymes such as glycosyltransferases.

The particular polypeptides which can be employed in the present invention are not critical thereto and can be any naturally occurring or synthetic polypeptide. Examples of the naturally occurring polypeptides which can be employed in the present invention include bovine serum albumin, keyhole limpet hemocyanin and egg ovalbumin.

The particular primary amino group containing lipids which can be employed in the present invention are not critical thereto. Examples of the primary amino group containing lipids which can be employed in the present invention include ceramide and long chain amines such as n-octadecylamine and n-hexadecylamine. Ceramides are the preferred primary amino group containing lipids employed in the present invention because they are normally attached to haptens in glycolipids.

The particular primary amino group containing supports which can be employed in the present invention are not critical thereto. Examples of the primary amino group containing supports which can be employed in the present invention include amino derived silica an amino-derived porous glass beads.

The A-associated H-antigens of the present invention are the immediate precursors to the repetitive A antigen (Type 3 chain A) illustrated below (see Clausen, H. et al, *Proc. Natl. Acad. Sci., U.S.A.*, 82:1199–1203 (1985), which has been found to be associated with the major $A_1$ subgroup:

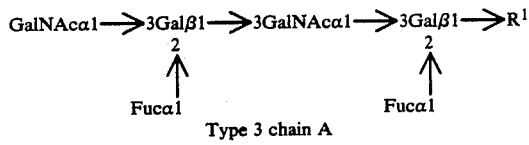

Type 3 chain A wherein $R^1$ represent a glycolipid and/or glycopeptide.

The A-associated H-antigens of the present invention are structurally distinct from other types of H antigens which are distributed in cells irrespective of blood group status as discussed below.

The major H antigens, which are distributed in various human tissue, including erythrocytes, irrespective of blood group ABO status include Type 1 chain H, Type 2 chain H (see Hakomori, S., *Semin. Hematol.*, 18:39–62 (1981); Type 3 chain H (O-linked) (see Donald, A. S. R., *Eur. J. Biochem.*, 120:243–249 (1981); and Type 4 chain H (Globo-H) (Kannagi, R. et al, *J. Biol. Chem.*, 258:8934–8942 (1983)).

Type 1 chain H, Type 2 chain H and Type 3 chain H, and Type 4 and chain H, all of which have the external Galβ1 component but lack the internal

GalNAcα1→3Galβ1 component, which is distinctive

of A antigens, are illustrated below:

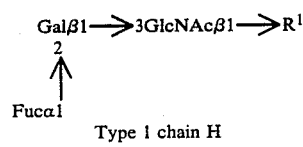

Type 1 chain H

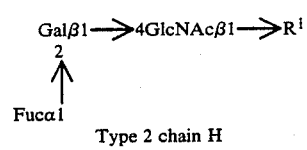

Type 2 chain H

-continued

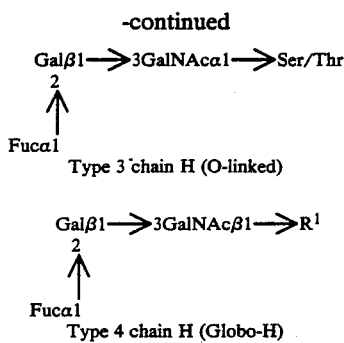

Type 3 chain H (O-linked)

Gal$\beta$1→3GalNAc$\beta$1→R$^1$
    2
    ↑
  Fuc$\alpha$1

Type 4 chain H (Globo-H)

wherein R$^1$ represents a glycolipid and/or glycopeptide.

The expression of Type 1 chain H in secretions is related to the H and Se genes while that of the Type 2 chain H is erythrocytes is dependent only on the H gene (see Kumazaki, T. et al, *Proc. Natl. Acad. Sci. U.S.A.* 82:4193–4197 (1984) and Graham, H. A. et al, *Human Blood Groups: 5th International Convocation on Immunology*, Buffalo, N.Y., (1976), Eds. Mohn, J. F. et al, pp. 257–267, Kager, Basel). The H-antigen in human erythrocytes is carried mainly on the Type 2 chain H variety. Type 3 chain H (O-linked) is mainly found on mucin type glycoproteins. Type 4 chain H (Globo-H), in contrast, is only found on glycolipids in tissue and erythrocytes (see Kannagi, R. et al, *FEBS Lett.*, 175:397–401 (1984). The quantity of H-antigen in various tissues is much-higher in blood group O than in blood group A or B individuals. Globo-H antigen is absent or present in only a very small quantity of blood group A$_1$ erythrocytes, while it is present in blood group A$_2$ erythrocytes in the same quantity as in blood group O erythrocytes (see Clausen, H. et al, *Biochem. Biophys. Res. Commun.*, 124:523–529 (1984)).

The A-associated H-antigens of the present invention, as described above, are therefore different from the previously known H-antigens.

The A-associated H-antigens can be isolated from blood group A or blood group AB erythrocytes or epithelial tissue. In general, this can be carried out by first obtaining a total lipid extract from the whole blood cells or epithelial tissue (see Kannagi, R. et al, *J. Biol. Chem.*, 257:14865–14874 (1982)).

Next, the glycolipid fraction is isolated from the total lipid extract (see Hakomori, S. et al, *Glycolipid Methodology*, pp. 13–47 Ed. Witting, L. A., American Oil Chemists Society, Champaign, Ill., (1976)).

Then, a neutral glycoprotein fraction is obtained from the glycolipid fraction (see Yu, R. K. et al, *J. Lipid Res.*, 13:680–686 (1972)).

Finally, the neutral glycolipid fraction is fractionated by low-pressure high performance liquid chromatography (hereinafter "HPLC") (see Watanabe, K. et al, *Biochem.*, 22:1020–1024 (1981) and Kannagi, R. et al, *J. Biol. Chem.*, 257:14865–14874 (1982)).

Location of A-associated H-antigens in the fractionated neutral glycolipid fraction can be ascertained by immunostaining with the monoclonal antibody MBr1 (see Clausen, H. et al, *Proc. Natl. Acad. Sci., U.S.A.*, 82:1199–1203 (1985) and Menard, S. et al, *Cancer Res.*, 43:1295–1300 (1983)).

A-associated H-antigens can also be obtained by the enzymatic degradation of the Type 3 chain A$^b$ having the following structure:

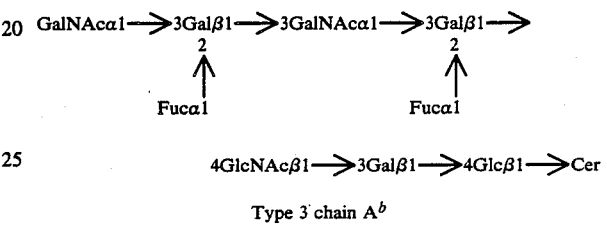

4GlcNAc$\beta$1→3Gal$\beta$1→4Glc$\beta$1→Cer

Type 3 chain A$^b$

Type 3 chain A$^b$ can be isolated as described in detail in Example 1 hereinafter. Hydrolysis of the terminal D-N-acetylgalactosamine can be carried out by incubating 200 $\mu$g of the glycolipid with 0.1 units/ml of $\alpha$-galactosaminidase (chicken liver, obtained by Dr. Jack Goldstein of the New York Blood Center) in a reaction mixture containing 100 $\mu$g of sodium deoxytaurocholate in 0.1 M acetic buffer (pH 4.5). Purification of the reaction product can then be carried out using reverse phase "Bond Elut" (C-18) column (Analytichem International, Harbor City, Calif.), DEAE sephadex and HPLC column chromatography successively as described in more detail in Example 1 hereinafter.

The A-associated H-antigens obtained by the above-described isolation procedures have the following glycosphingolipid structure:

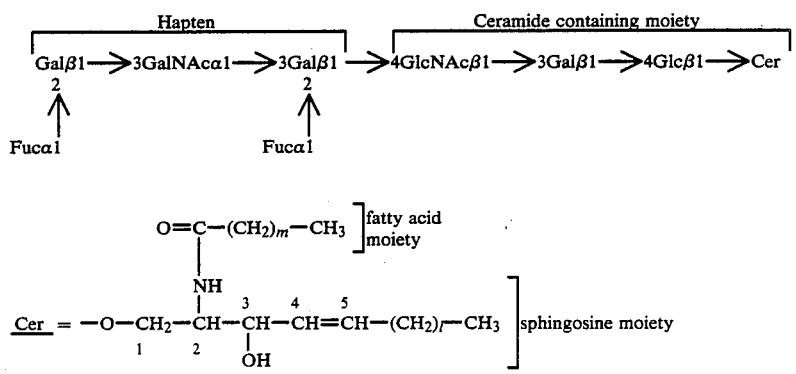

where m=12–24 (the acyl group may contain unsaturations and/or $\alpha$-OHs) and l=24 or 14

The hapten of the A-associated H-antigen can be obtained from the above glycosphingolipid structure and linked to the variable carrier by a variety of well known methods.

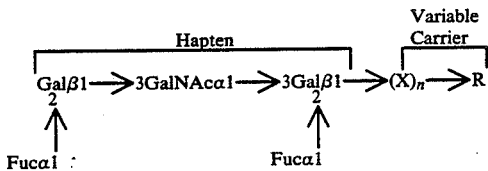
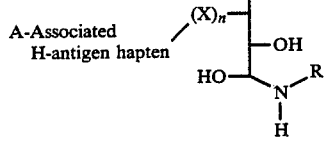

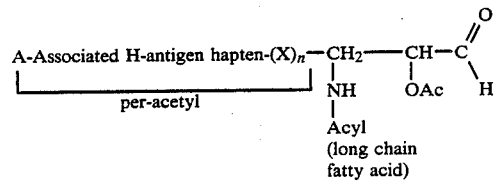

The simplest method of removing the ceramide containing moiety, in whole or in part, from the glycosphingolipid, is by providing an intact sugar residue, e.g., the terminal galactose of the hapten when n=0 or the terminal sugar residue when n is greater than 0, or a simple reactive intermediate thereof, which can be coupled via well known reaction sequences to a suitable material such as a polypeptide, a primary amino group containing lipid or a primary amino group containing support (R). Two examples of this procedure are described below:

(1) The neutral glycolipid is first selectively oxidized at the 3-position of the sphingosine (see Kishimoto, Y. et al, *Arch. Bichem. Biophys.*, 161:426–434 (1974); Iwamori, M. et al, *Biochem. Biophys. Acta.*, 380:308–319 (1975); and Iwamori, M. et al, *J. Lipid Res.*, 16:332–336 (1975)). More specifically, the glycosphingolipid is dissolved, at a final concentration of 10 mg/ml, in dioxane or tetrahydrofuran and then reacted with a molar excess of about 20:1 to 50:1 of 2,3-dichloro-5,6-dicyanobenzoquinone to glycosphingolipid at 37°±5° C. for about 24 hrs. The resulting 3-keto-glycosphingolipid is isolated using low pressure chromatography on silica using chloroform/methanol (2:1 (v/v)) as the mobile phase or HPLC on silica using isopropyl alcohol/hexane/water in a gradient of 55:40:5 (v/v/v) to 55:20:25 (v/v/v). Next, the isolated 3-keto-glycosphingolipid is treated under very mild basic conditions to release the free reducing oligosaccharide by $\beta$-elimination (chloroform/0.01 N Na$_2$CO$_3$ in methanol (2:1 (v/v)) at 37°±5° C. for 1 hour (see Iwamori, M. et al., *Chem. Phys. Lipids*, 20:193–203 (1977) or 0.5 N triethylamine in chloroform/methanol (2:1 (v/v)) at 37°±5° C. for about 1 hour (see Schengrund, C. -L. et al., *Fed. Proc.*, 45:1821 (1986)).

The resulting oligosaccharide can then be bonded, via its reducing end, to any suitable primary amino group containing material, e.g., a polypeptide such as bovine serum albumin, a primary amino group containing support such as an amino derived silica or porous glass beads, or a primary amino group containing lipid such as n-octadecylamine or n-hexadecylamine, by reductive amination using 10:1 to 50:1 molar excess of sodium cyanoborohydride in an aqueous solvent. This reaction mechanism is illustrated below.

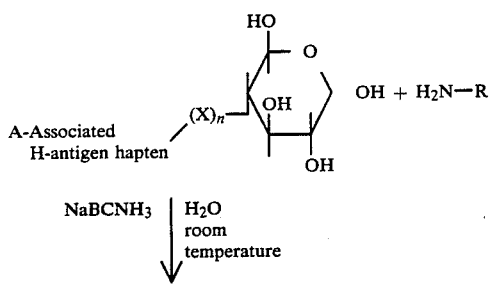

(2) In a second procedure, the glycosphingolipid is per-acetylated with a greater than 500 molar excess of pyridine/acetic anhydride (2:1 (v/v)) at room temperature overnight or at about 80° C. for 1 hr. The double bond of the sphingosine is then cleaved using 0.2 M periodic acid in methanol and 5.0% (w/v) osmium tetroxide in diethyl ether. Then, 1–3 mg of the acetylated glycolipid is evaporated to dryness under N$_2$ using toluene to azeotrope off the excess pyridine and acetic anhydride. The resulting product is taken up in 0.5 ml of methanol and then 0.2 ml of 0.2 M periodic acid in methanol is added, followed by the addition of 25 ml of 5.0% (w/v) of osmium tetroxide in diethyl ether. The mixture is left at 5° C. overnight and excess reagent is destroyed with a drop of glycerol. Then, 6.0 ml of chloroform/methanol (2:1 (v/v)) and 1.5 ml water are added, the organic phase is collected and washed four times with 2.5 ml of chloroform/methanol/water (1:10:10 (v/v/v)) and then dried under a N$_2$ stream (see MacDonald, D. L. et al., *J. Lipid Res.*, 21:642–645 (1980)). The resulting derivative has the following structure:

The treatment of this aldehyde using 50 μl of 0.2 M sodium methoxide in 0.3 ml of methanol de-O-acetylates the oligosaccharide moiety and simultaneously frees it, by a base catalyzed migration of the aldehyde double bond followed by $\beta$-elimination. The resulting oligosaccharide can then be coupled, as described above, to a suitable polypeptide, primary amino group containing lipid or primary amino group containing support.

Alternately, the aldehyde acetate can be oxidized with performic acid to an acid form. More specifically, the acetylated glycolipid aldehyde is treated with performic acid prepared by mixing 15 ml of 30% (v/v) hydrogen peroxide with 1.0 ml of 80% (v/v) formic acid, which is allowed to stand for two hours. 0.2 ml of this reagent is added to the acetylated glycolipid aldehyde and allowed to stand for about 20 hrs at room temperature (see MacDonald, D. L. et al., *J. Lipid Res.*, 21:642–645 (1980)). The resulting product can then be coupled to a suitable polypeptide, primary amino group containing lipid or primary amino group containing support with N-hydroxy-succinimide and dicyclohexylcarbodiimide in dioxane, followed by de-O-acetylation with sodium methoxide in methanol. More specifically, 10 mg of acetylated glycolipid acid is dissolved in 1.0 ml of dioxane. The activated ester is formed by adding 5.0 mg of N-hydroxy succinimide dissolved in 0.5 ml of dioxane plug 5.0 mg of dicyclohexylcarbodiimide dissolved in 1.0 ml of dioxane. The resulting mixture is incubated at 15°±1° C. for 30 min. Then, 1.0 g of alkylamine glass beads (Corning CPG-1350) or equivalent material containing 60 μeq of $NH_2$ groups per gram and 5.0 ml dioxane are added and mixed gently at room temperature for about 72 hours. One drop of glacial acetic acid is then added to derivatize the remaining amino groups on the glass beads and mixing is continued for about 24 hours. After washing the glass with dioxane, the glass immobilized glycolipid is suspended in 10 ml chloroform/methanol (2:1 (v/v)) and 2.0 ml of 0.5% (w/v) sodium methoxide in methanol are added. After 30 minutes at room temperature, the glass is filtered and washed with chloroform/methanol (2:1 (v/v)), washed with water and washed with phosphate buffer (pH 7.0). The glass beads can then be stored in phosphate buffer (pH 7.0) containing sodium azide. The resulting complex has the following structure:

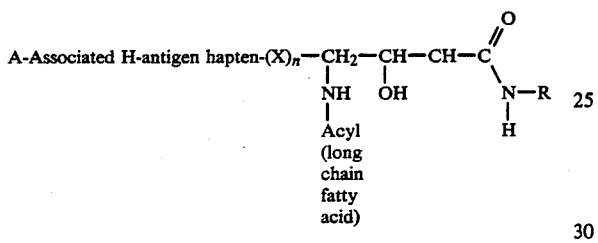

(see Young, W. W. et al., *J. Lipid Res.*, 20:275–278 (1979)).

The per-o-acetylated glycolipid acid can also be produced directly from the glycosphingolipid, following per-o-acetylation, by treatment with potassium permanganate in acetone at room temperature overnight (see MacDonald, D. L. et al., *J. Lipid Res.*, 21:642–645 (1980)).

In a second embodiment of the present invention, the A-associated H-antigens of the present invention can be used to develop monoclonal antibodies for use in blood typing. The monoclonal antibodies can be prepared by well known means as described in Kohler, G. et al., *Nature*, 256:495–496 (1975) and Clausen, H. et al., *Biochem.*, 24:6190–6194 (1985).

Monoclonal antibodies directed to the A-associated H-antigens, can be used alone or in combination with other anti-A antibodies for identification of blood group A erythrocytes including minor A subgroups. Blood typing can be carried out according to standard blood banking methods (see Kabat, E. A. et al., *Experimental Immunochemistry,* 2d Ed., Thomas Publishers, Springfield, Ill. (1967)). This involves an agglutination test where the antibody is incubated with a patient's erythrocytes for varying times and at different temperatures. Agglutination, i.e., clustering of cells due to specific antigen-antibody reactions, is thereafter observed macroscopically (see *Clausen,* H. et al., *Proc. Natl. Acad. Sci., U.S.A.*, 82:1199–1203 (1985)).

The monoclonal antibodies can also be employed in other immunoassays for identification of blood groups. For example, immunohistology of epithelial tissues where antigens can be localized in relation to epithalial architecture (see Dabelsteen, E. et al., *J. Invest. Dermatol.*, 82:13–17 (1984)); immune inhibition of cellular secretions such as saliva, gastric and pancreatic juices (see Kabat, E. A. et al., *Experimental Immunochemistry,* 2nd Ed., Thomas Publishers, Springfield, Ill. (1967)); and immuno detection of blood group antigens for detailed identification in forensic medicine using, for example, semen and/or sperm cells (see Hartman, G., "Group Antigens in Human Antigens," Thesis. Munksgaard, Copenhagan (1941)).

It is important to note that the A-associated H-antigens of the present invention are relatively abundant in the minor A subgroups and that antibodies directed towards these antigens should preferentially detect minor blood group A erythrocytes. It is therefore desirable to include antibodies directed to other A antigens, i.e., Type 2 chain A-antigen and Type 3 chain A-antigens, which are relatively abundant on the major A subgroups in a test for blood group A typing. (see *Clausen,* H. et al., *Proc. Natl. Acad. Sci.,* U.S.A., 82:1199–1203 (1985) and *Clausen,* H. et al., *Biochem.*, 24:6190–6194 (1985)).

The following examples are provided for illustrative purposes only and are in no way intended to limit the scope of the present invention. Unless otherwise indicated, all parts, percents, ratios and the like are by weight.

EXAMPLE 1

(A) Isolation of A-associated H-Antigens

For purification of A-associated H-antigens, pooled outdated human whole type A blood was lysed in ice-cold tap water containing 0.2% of acetic acid and whole blood cell membranes, including those of white cells, were prepared by continuous centrifugation on a Sharpless centrifuge. The total lipids were extracted with isopropyl alcohol/hexane/water (55:25:20 (v/v/v)) (see Kannagi, R. et al., *J. Biol. Chem.*, 257:14865–14874 (1982)). The total lipid extract was evaporated to dryness in a rotary evaporator. The residue was dissolved in 5 volumes, to the original packed cell volume (v/v), with chloroform/methanol (2:1 (v/v)) and solvent-partitioned after addition of 1/6 volumes of water by a modified Folch's method (see Hakomori, S. et al., *Glycolipid Methodology,* pp. 13–47, Ed. Witting, L. A. American Oil Chemists Society, Champaign, Ill. (1976)). The upper phase glycolipid fraction was separated and solvent-partitioned three times as described above. Thereafter, the upper phase glycolipid fraction was evaporated to dryness and dialyzed through a Spectraper 3 dialysis tube (Spectrum Medical Industries, Los Angeles, Ca.) against deionized water (see Hakomori, S. et al., *Glycolipid Methodology,* pp. 13–47, Ed. Witting, L. A., American Oil Chemists' Society, Champaign, Ill. (1976)).

Neutral glycolipids were separated from the total upper phase glycolipid fraction by DEAE-Sephadex (A-25) chromatography using chloroform/methanol/water (30:60:80 (v/v/v)) (see Yu, R. K. et al., *J. Lipid Res.*, 13:680–686 (1972)). The neutral glycolipid fraction was further fractionated by HPLC on a 1×50-cm column of Iatrobeads 6RS-8060 (60 μm particles; Iatron Chemical Co., Tokyo, Japan) (see Watanabe, K. et al., *Biochem.*, 22:1020–1024 (1981) and Kannagi, R. et al., *J. Biol. Chem.*, 257:14865–14874 (1982)). The elution was programmed with 55:40:5 (v/v/v) to 55:20:25 (v/v/v) isopropyl alcohol/hexane/water for 200 min with a flow rate of 3 ml/min. Each 6 ml fraction was collected on a fraction collector (total of 600 ml of eluent collected over 100 fractions).

Each fraction was then analyzed by high performance thin-layer chromatography (hereinafter "HPTLC") in a solvent of chloroform/methanol/water (56:38:10 (v/v/v)) and the A-associated H-antigens were identified by immunostaining with monoclonal antibody MBrl (see Clausen, H. et al., *J. Biol. Chem.*, 261:1380–1387 (1986)). MBrl was obtained from Professors Sonnino Ricardo Ghidoni and Maria Colnaghi of the Division of Experimental Oncology, Instituto Nazionale per la Ricerca sul Cancro, Milan, Italy (see Menard, S. et al., *Cancer Res.*, 43:1295–1300 (1983)). The MBrl antibody specifically reacts with the following structure:

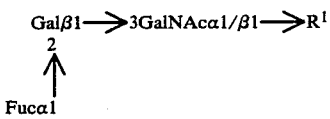

wherein $R^1$ represents a glycolipid and/or glycopeptide.

As a result, MBrl antibody reacts with Type 3 chain H and Type 4 chain H-antigens including the A-associated H-antigens of the present invention but not with Type 1 chain H or Type 2 chain H-antigens (see Brenner, E. G. et al., *J. Biol. Chem.*, 259:14773–14777 (1984). Clausen, H. et al., *Proc. Natl. Acad. Sci., U.S.A.*, 82:1199–1203 (1985) and Clausen, H. et al., *J. Biol. Chem.*, 261:1380–1387 (1986)).

HPTLC-immunostaining was performed as described in Magnani, J. L. et al., *Anal. Biochem.*, 109:399–402 (1980). More specifically, after the neutral glycolipids had been separated on HPTLC (Baker J. T.-HPFTLC Plate, J. T. Baker Chemical Co., Philipsburg, N.J.) as described above, the plates were blocked by immersion in 5% (w/v) bovine serum albumin followed by sequential incubation with MBrl, rabbit anti-mouse Ig and $^{125}$I-protein A. The plates were then subjected to autoradiography.

By this method it was found that fractions 54 and 55 contained A-associated H-antigens, as well as Type 2 chain H$_2$ illustrated below. Type 2 chain A$^b$ illustrated below and Type 3 chain A$^b$ illustrated below.

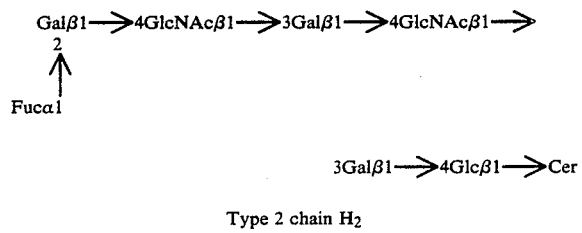

Type 2 chain H$_2$

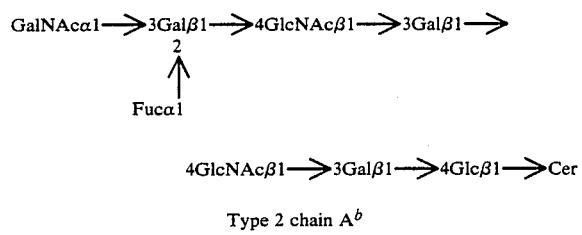

Type 2 chain A$^b$

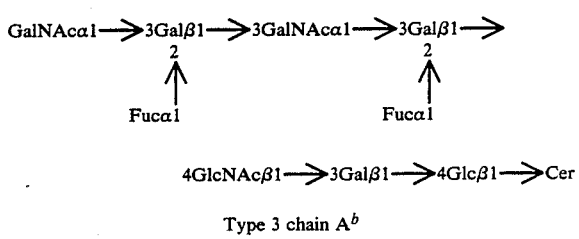

Type 3 chain A$^b$

Fractions 54 and 55 described above were then rechromatographed on high-pressure HPLC through Iatrobeads 6RS-8010 column using a gradient of isopropyl alcohol/hexane/water from 55:38:7 (v/v/v) to 55:30:15 (v/v/v) (see Watanabe, K. et al., *Biochemn.*, 22:1020–1024 (1981) and Kannagi, R. et al., *J. Biol. Chem.*, 258:8934–8942 (1983)). The total volume of the eluent was 200 ml and was collected over 200 fractions for 200 min (1.0 ml/min/fraction). Fractions 54 and 55 containing only A-associated H-antigens and Type 2 chain H$_2$ was acetylated and A-associated H-antigens were identified by two-dimensional HPTLC-immunostaining with MBrl antibody after deacetylation in situ.

Acetylation was performed in pyridine/acetic acid (2:1 (v/v)) at room temperature for 18 hours and the acetates (see Saito, T. et al., *J. Lipid. Res.*, 12:257–259 (1971)) were separated on HPTLC plates in dichloroethane/acetone/water (50:50:0.1 (v/v/v) in a first direction and dichloroethane/acetone/water (50:50:1.0 (v/v/v) in a second direction. Deacetylation was conducted directly on the plates by incubating the plates with 0.2% (w/v) sodium methoxide in methanol. Then, immunostaining was carried out using monoclonal antibody MBrl as described in Clausen et al., *Proc. Natl. Acad. Sci., U.S.A.*, 82:1199–1203 (1985)).

The A-associated H-glycolipids so identified were thereafter purified by preparative HPTLC on Merck HPTLC plates (Silica Gel 60 Merck) in a solvent of dichloroethane/acetone/water (50:50:0.1 (v/v/v). The location of glycolipids on HPTLC was detected by Primulin spray (Aldrich) followed by observation under UV light (see Skipski, V. P., *Methods Enzymol.*, 34:396–425 (1975)). The acetylated components were then extracted in chloroform/methanol/water (2:1:0.15 (v/v/v)) and deacetylated in chloroform/methanol (2:1 (v/v)) containing 0.2% (w/v) sodium methoxide in methanol at room temperature for 15 min (see Saito, T. et al., *J. Lipid Res.*, 12:257–259 (1971).

(B) Characteristics of A-associated H-antigens (1) HPTLC Mobility and Enzymatic Degradation In order to obtain structural information of the glycolipids, HPTLC immunostaining with monoclonal antibodies was performed before and after successive enzymatic degradation (see Clausen, H. et al., *J. Biol. Chem.*, 261:1380–1387 (1986)).

The monoclonal antibodies employed for HPTLC immunostaining were 1B2 (see Young, W. W. et al., *J. Biol. Chem.*, 256:10967–10972 (1981)), anti-T (Chembiomed, Inc., Edmonton, Alberta, Canada) and AH16 monoclonal antibodies (see Abe, K. et al., *J. Immunol.*, 132:1951–1954 (1984)).

Monoclonal antibodies 1B2, anti-T and AH16 have binding specificity for the following structures, respectively:

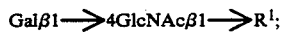

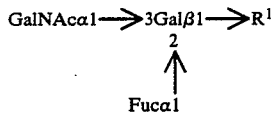

wherein $R^1$ represents a glycolipid and/or glycopeptide.

The enzymes used for the enzymatic degradation were bovine liver α-L-fucosidase (Sigma Co.) and β-galactosidase of *Charonia lampas* (Seikagaku Kogyo Co., Ltd., Tokyo, Japan). Hydrolysis was performed by incubation of 10 μg of glycolipid in 20 μl of 0.1 unit/ml of enzyme in the presence of 30 μg of sodium deoxytaurocholate in 0.1 M acetate buffer (pH 4.5) (see Hakomori, S. et al., *J. Biol. Chem.*, 246:2271–2277 (1971)).

In order to prepare a large quantity of galactosyl $A^a$, i.e., A-associated H-antigens defucosylated only at the terminal fucose, which was later used for ($^1$H NMR) spectroscopy (see below), a large quantity (200 μg) of A-associated H-antigens obtained from A erythrocytes was hydrolyzed with α-L-fucosidase as described above. After hydrolysis, the reaction mixture was run over a reverse phase "Bond Elut"(C-18) column (Analytichem International, Harbor City, Calif.), DEAE-Sephadex, and HPLC, successively. The reaction mixture was poured over a "Bond Elut" column, washed with distilled water and eluted with methanol. DEAE-Sephodex and HPLC column chromatography was then carried out as described above. The final glycolipid preparation was free of salt, detergent and protein.

The A-associated H-antigens obtained from A erythrocytes were characterized as having a slightly slower HPTLC mobility than Type 2 $H_2$ but faster than Type 2 chain $A^b$. The A-associated H-antigens obtained from A erythrocytes were degraded by bovine liver α-L-fucosidase to a component with the same HPTLC mobility as globo-H antigen (see Kannagi, R. et al., *FEBS Lett.*, 175:397–401 (1984)), which was not reactive with 1B2 and anti-T monoclonal antibodies on HPTLC immunostaining, whereas Type 2 chain $H_2$ was stained by 1B2 after defucosylation. Further, degradation of A-associated H-antigens obtained from A erythrocytes was found to be very difficult and they were only partially degraded by β-galactosidase of *C. lampas*, although a complete cleavage was possible by repeated incubation. The β-Gal residue attached to the β-Gal-NAc residue of the globoside was also resistant to various β-galactosidases (see Kannagi, R. et al., *J. Biol. Chem.*, 258:8934–8942 (1983)). The degradation product after β-galactosidase showed the same HPTLC mobility as $A^1$ glycolipid, and in addition, was stained by AH16 monoclonal antibody, indicating that A-associated H-antigens obtained from A erythrocytes contain an internal $A^a$ structure.

(2) Nuclear Magnetic Resonance Spectra

Proton nuclear magnetic resonance ($^1$H NMR) spectra of the isolated glycolipids were recorded at 500 MHz with a Bruker WM-500 spectrometer equipped with an Aspect 2000 computer and pulse programmer, operating in the Fourier transform mode with quadrature detection. The spectra were recorded at 308±and 328±2K on deuterium-exchanged samples (200–400 μg) dissolved in 0.4 ml of dimethyl sulfoxide/$d_6$ containing 2% (v/v) $D_2O$ (see Dabrowski, J. et al., *Biochem.*, 19:5652–5658 (1980)) and 1% (v/v) tetramethylsilane as a chemical shift reference. 3000–4000 free induction decays were collected for each spectrum using parameters and the data treated as described in Bremer, E. G. et al., *J. Biol. Chem.*, 259:14773–14777 (1984). (see FIGS. 1A and 1B).

Figure 1B:
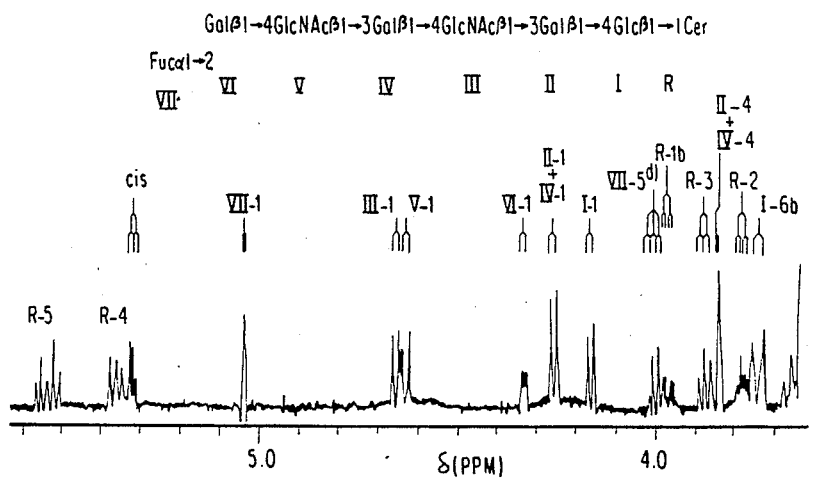
FIG. 1B is the downfield region of a resolution enhanced ($^1$H NMR) spectra, at 308°±2° K., of Type 2 chain $H_2$ obtained from O erythrocytes.

In FIGS. 1A and 1B, the Arabic numerals refer to protons of residues indicated by the Roman numerals in the structures drawn above the spectra. Resonances marked by "R-" are from sphingosine backbones, while triplets marked "cis" are from cis-vinyl protons of unsaturated fatty acids. In FIGS. 1A and 1B, the footnotes have the following meaning: $^a$α-GalNAc H-1, H-2 connectivity was confirmed by continuous irradiation decoupling; $^b$α-Fuc H-5 was established by decoupling from the Me doublet at 1.099 ppm ($^3J_{5,6}=6.7$ Hz); $^c$α-Fuc H-5 was established by decoupling from the Me doublet at 1.066 ppm (the assignment is based on the fact that the resonance designated V-5 shows relatively small displacements in the series Type 2 chain $A^a$ through Type 3 chain $A^b$, while this resonance (VIII-5) is absent when the terminal Fucα1->2 is removed (see FIG. 2), and shifts to 4.237 ppm upon addition of a terminal GalNAcα1->3 residue (see Clausen, H. et al., *Proc. Natl. Acad. Sci., U.S.A*, 82:1199–1203 (1985) and Table II); in addition, the shift 4.060 ppm is close to the values found for Type 1 chain $H_1$ (4.072 ppm reported at 308±2 K and 4.07 ppm reported at 338 K by Dabrowski, J. et al., *Arch. Biochem. Biophys.*, 210:405–411 (1981)) and for globo-H (4.07 ppm reported at 302 K by Kannagi, R. et al., *J. Biol. Chem.*, 258:8934–8942 (1983)), and is therefore consistent with the structure Fucα1->2Galβ1->3HexNAc); $^d$α-Fuc H-5 was established by decoupling from the Me doublet at 1.068 ppm; $^f$tentative assignments. The results are summarized in Tables I and II below.

TABLE I

Glycosyl H-1 chemical shifts (ppm from tetramethylsilane) and $^3J_{1,2}$ coupling constants (Hz) of Type 2 and Type 3 chain glycosphingolipids in dimethyl sulfoxide-$d_6$ at 308 ± 2K

| | GalNAcα1→3 | | GalNAcα1→3 | | Galβ1→4GlcNAcβ1→3Galβ1→4GlcNAcβ1→3Galβ1→4Glcβ1→1Cer | | | | |
|---|---|---|---|---|---|---|---|---|---|
| | Fucα1→2 | Galβ1→3 | | Fucα1→2 | | | | | |
| Type 2 | | | | | | | | | |
| 1. nLc$_4$ | | | | | 4.211(6.7) | 4.664(8.5) | | 4.261(7.3) | 4.168(7.9)$^a$ |
| 2. nLc$_6$ | | | | | 4.208(6.1) | 4.652(8.5) | | 4.260(.3) | 4.169(7.9)$^b$ |
| 3. H$_1$ | | | | 5.039(3.0) | 5.335(7.3) | 4.629(7.9) | | 4.258(7.3) | 4.168(7.3)$^a$ |
| 4. H$_2$ | | | | 5.040(3.0) | 4.335(7.3) | 4.630(7.9) | 4.260(7.3) | 4.258(7.3) | 4.168(7.3) |
| 5. A$^a$ | | | 4.935(4.3) | 5.149(3.7) | 4.387(7.9) | 4.620(7.3) | 4.258(7.3) | 4.258(7.9) | 4.172(7.3)$^c$ |
| 6. A$^b$ | | | 4.933(3.7) | 5.146(4.3) | 4.383(7.9) | 4.616(7.3) | 4.258(7.3) | 4.258(7.3) | 4.169(7.3) |
| Type 3 | | | | | | | | | |
| 7. Galβ1→3A$^a$ | | 4.304(7.3) | 5.029(3.7) | 5.218(4.3) | 4.378(7.9) | 4.628(7.9) | | 4.260(7.3) | 4.170(7.3) |
| 8. A-associated H antigen | 4.926(3.0) | 4.548(7.3) | 5.055(3.0) | 5.228(4.3) | 4.356(7.9) | 4.625(7.9) | | 4.260(7.3) | 4.170(7.9) |
| 9. A$^b$ | 4.947(4.3)$^d$ | 5.061(3.7) | 4.663(7.9) | 4.955(4.3)$^d$ | 5.329(4.3) | 4.344(7.9) | 4.618(7.3) | 4.260(7.3) | 4.168(7.9) |

$^a$Data in agreement with Dabrowski, J. et al, Arch. Biochem. Biophys., 210: 405-411 (1981)
$^b$Data in agreement with Dabrowski, U. et al, J. Biol. Chem., 259, 7648-7651 (1984)
$^c$These values differ from those in Clausen, H. Et al, Biochem., 24:3578-3586 (1985) because a more dilute solution was used here. Several resonances in the short chain A$^a$ are sensitive to concentration, including the NAc methyl and Fuc H-5,6 shifts given in Table II.
$^d$Assignment may be reversed.

TABLE II

Fucosyl H-5,6, GalNAc H-2, and HexNAc NAc chemical shifts (ppm from tetramethylsilane) for Type 2 and Type 3 chain glycosphingolipids in dimethyl sulfoxide-$d_6$ at 308 ± 2K

| | GalNAc$\alpha$1->3 | | Fuc$\alpha$->2 | | GalNAc$\alpha$1->3 | | Fuc$\alpha$1->2 | | GlcNAc$\beta$1->3, |
|---|---|---|---|---|---|---|---|---|---|
| | H-2 | NAc | H-5 | CH$_3$ | H-2 | NAc | H-5 | CH$_3$ | NAc |
| Type 2 | | | | | | | | | |
| 1. nLc$_4$ | | | | | | | | | 1.817 |
| 2. H$_1$ | | | | | | | 4.007 | 1.068 | 1.818 |
| 3. A$^a$ | | | | | 4.105 | 1.849 | 4.144 | 1.081 | 1.824 |
| Type 3 | | | | | | | | | |
| 4. Gal-A$^a$ | | | | | 4.223 | 1.826 | 4.149 | 1.081 | 1.819 |
| 5. A-associated H antigen | | | 4.060 | 1.099 | 4.133 | 1.811 | 4.125 | 1.066 | 1.819 |
| 6. A$^b$ | ND$^a$ | 1.843 | 4.237 | 1.024 | 4.084 | 1.843 | 4.104 | 1.076 | 1.818 |

$^a$ND, not determined.

The ($^1$H NMR) spectrum of the A-associated H-antigens obtained from A erythrocytes was characterized by the unusual presence of three $\alpha$-anomeric resonances ($^3J_{1,2}$=3-4 Hz) in addition to five resonances from $\beta$-anomeric protons ($^3J_{1,2}$=7-9 Hz). (see FIG. 1A and Table I). The signal at 5.055 ppm was identified as arising from an $\alpha$-GalNAc residue by decoupling from its readily identifiable H-2 resonance at 4.135 ppm ($^3J_{1,2}$3.7 Hz, $^3J_{2,3}$=11.0 Hz) see Clausen, H. et al., *Proc. Natl. Acad. Sci., USA*, 82:1199-1203 (1985); Dabrowski, J. et al., *Biochem.*, 19:5652-5658 (1980) and Clausen, H. et al., *Biochem.*, 24:3578-3586 (1985)). The identity of the other two $\alpha$-anomeric resonances can be inferred from the presence of two sets of $\alpha$-Fuc H-5 and CH$_3$ ($^3J_{5,6}$=6.7 Hz) resonances in the spectrum (see Table II).

After removal of the terminal $\alpha$-Fuc residue by $\alpha$-fucosidase (see above), the major changes in the ($^1$H NMR) were observed to be: (a) the disappearance of the more upfield $\alpha$-Fuc H-1, along with the H-5 signal at 4.060 ppm and the CH$_3$ signal at 1.099 ppm, and (b) the large upfield shift of one $\beta$ H-1 signal from 4.548 to 4.304 ppm, which is therefore assigned as rising from the terminal Gal residue in the newly formed structure (see FIG. 2).

Figure 2:
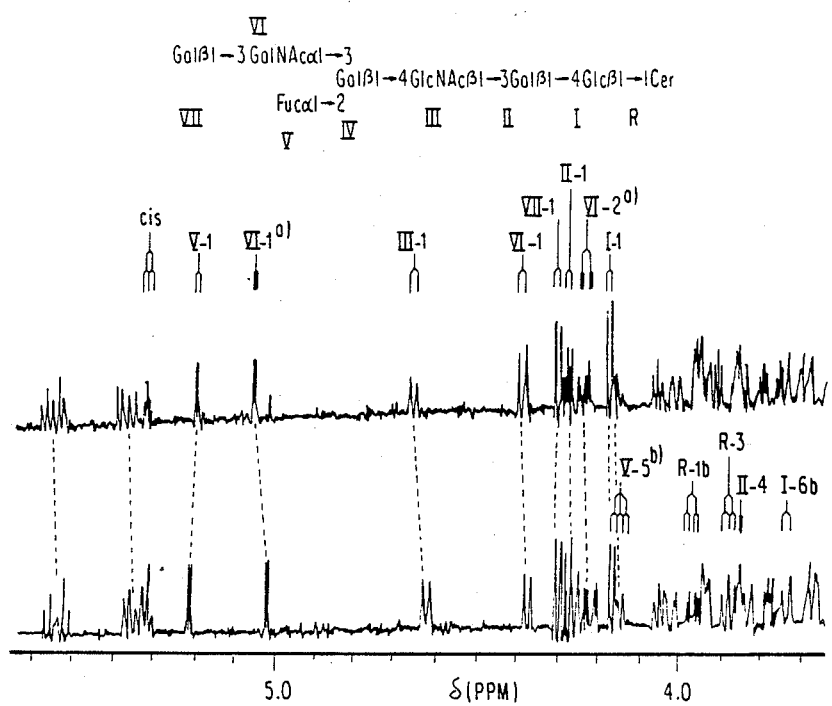
FIG. 2 is the ($^1$H NMR) spectra of the structure of A-associated H-antigens which is produced by treatment of approximately 200 μg of A-associated H-antigens obtained from A erythrocytes with α-L-fucosidase.
Figure 3A:
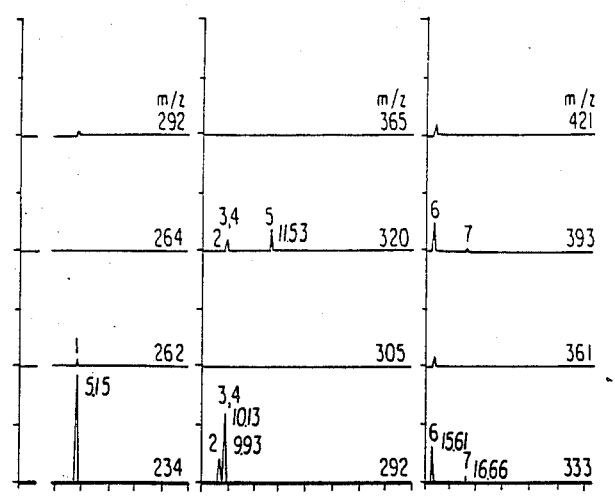
FIG. 3A is selected ion chromatograms of partially O-methylated alditol and hexosaminitol acetates from the hydrolysate of permethylated A-associated H-antigens obtained from A erythrocytes which have been separated on a DB-5 capillary column (temperature programmed from 140° to 250° C. at 4° C./min).
Figure 3B:
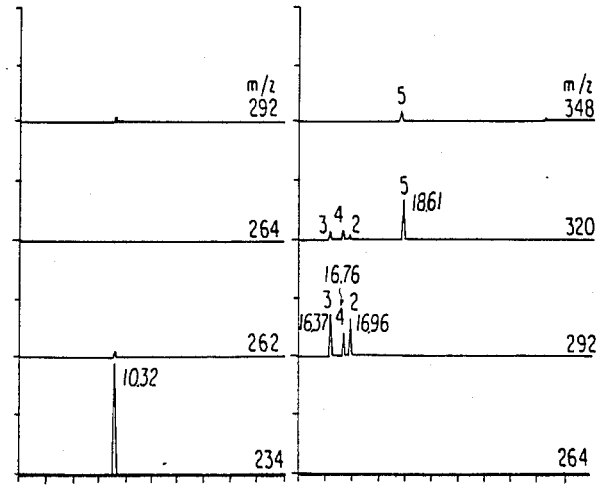
FIG. 3B is selected ion chromatograms of partially O-methylated alditol and hexosaminitol acetates from the hydrolysate of permethylated A-associated H-antigens obtained from A erythrocytes which have been separated on a DB-225 capillary column (temperature programmed from 130° to 220° C. at 4° C./min).

In FIG. 2, the lower spectrum was obtained at 380±2K and the upper spectrum was obtained at 328±2K. In FIG. 2, the footnotes have the following meaning: $^a$$\alpha$-GalNAc H-1, H-2 connectivity was confirmed by continuous irradiation decoupling; $^b$$\alpha$-Fuc H-5 was established by decoupling from the Me doublet at 1.081 ppm. The resonance at 4.278 ppm (308 K, lower spectrum) is a quartet (J=7.3 Hz) of very narrow line width, and is therefore believed to arise from an impurity.

Furthermore, the spectrum of the defucosylated compound is readily interpreted as the addition of 1 $\beta$-Gal residue to Type 2 chain A$^a$ (see Clausen, H. et al., *Biochem.*, 24:3578-3586 (1985)), and the anomeric signals assigned on that basis. (see Table I). The large downfield shift of the terminal $\beta$-Gal H-1 resonance on $\alpha$1->2 fucosylation is expected for the Gal$\beta$1->3HexNAc structure, as seen for Type 1 chain lacto- (see Dabrowski, J. et al., *Arch. Biochem. Biophys.*, 210:405-411 (1981)) and globo H-series (see Kannagi, R. et al., *J. Biol. Chem.*, 258:8934-8942 (1983)) glycolipids. In this case, however, the $\alpha$-, as opposed to $\beta$-, HexNAc H-1 experiences a slight deshielding, and moves to somewhat lower field rather than higher, in contrast to those structures. The terminal $\alpha$-Fuc H-1 of A-associated H-antigens obtained from A erythrocytes appear rather upfield, resembling most of all the shift for globo H-series (see Kannagi, R. et al., *J. Biol. Chem.*, 258:8934-8942 (1983); Bremer, E.G. et al., *J. Biol. Chem.*, 259:14773-14777 (1984) and Kannagi, R. et al., *FEBS Lett.*, 175:397-401 (1984)). An interesting feature is the unexpected downfield shift of the core (internal) $\alpha$-Fuc H-1 signal, beginning with the addition of the $\beta$-Gal residue to the A$^a$ glycolipid. The shift chain of the proton upon substitution of another residue ($\alpha$-Gal-NAc) is not normally encountered unless some unusual inter-residue interactions are present, i.e., steric crowding causing repositioning of an anisotropic group such as NAc, confirmational change at glycocidic linkages, or a unique confirmational preference which brings an oxygen atom of the newly added residue in contact with the proton in question. In addition, this resonance shows a negative temperature-shift coefficient, which is preserved in the H structure, and Type 3 chain A$^b$, helping to confirm the assignment (see FIG. 2) (see Clausen, H. et al., *Proc. Natl. Acad. Sci., USA*, 124:523-529 (1984)).

Comparison with the data for Type 3 chain A$^b$ also helped confirm the assignments for the A-associated H-antigen spectrum (see Tables I and II). Thus, the addition of the terminal GalNAc$\alpha$1->3 residue is manifested by (a) an additional $\alpha$-signal in the downfield region; (b) an additional NAc signal; (c) expected downfield shifts for the subterminal $\beta$-Gal H-1 and terminal $\alpha$-Fuc H-1 and H-5 resonances (see Clausen, H. et al., *Biochem.*, 24:3578-3586 (1985)); and (d) a larger than expected upfield shift for the core $\alpha$-GalNAc H-1 ($\Delta\delta$=−0.10 ppm; for $\beta$-GlcNAc H-1 of Type 2 chain, $\Delta\delta$=−0.01 ppm, H->A conversion). There are measurable upfield shift changes for the core $\beta$-Gal H-1 as the outer, A-associated H-antigen, terminal is added and elaborated. Furthermore, there is a relatively large downfield shift ($\Delta\delta$=−0.10 ppm) of the core $\alpha$-Fuc H-1 upon addition of the terminal GalNAc$\alpha$1->3 to make Type 3 chain A$^b$. This may be the most extreme "long-range" effect seen to date for a glycolipid, and can be taken as indicative of some unusual inter-residue interactions as discussed above.

By comparison, the ($^1$H NMR) spectrum of Type 2 chain H$_2$ (see FIG. 1B) is straightforward and easily interpretable in terms of the insertion of an additional N-acetyllactosamine unit into H$_1$, or as $\alpha$1->2 fucosylation of norhexosylceramide (see Table I) with expected shifts of the outer $\beta$-Gal and -62 -GlcNAc anomeric protons (see Dabrowski, J. et al., *Arch. Biochem. Biophys.*, 210:405-411 (1981)).

A notable feature is the additional splitting of the suterminal $\beta$-Gal H-1 into an unusual triplet-like structure characteristic of virtual coupling (see Musher, J. I. et al., *Tetrahedron*, 18:791-809 (1962)). This phenome- (1985). More specifically, 2 μg of the A-associated H-antigens coated on acid treated *Salmonella sp.* serotype minnesota were used for immunization of one BALB/c mouse (3 months old). The mouse received five injections with 5-7 day intervals therebetween. Three days after the last injection, the spleen was removed from the mouse and the spleen cells were fused with SP/2-O as described in Clausen, H. et al., *Biochem.*, 24:6190–6194 (1985). Hybridomas were screened by a solid-phase radioimmunoassay using the A-associated H-antigens obtained from A erythrocytes and a panel of control glycolipids In the radioimmunoassay, the initial glycolipid concentration was 100 ng, with 300 ng of cholesterol and 500 ng of lecithin. The monoclonal antibodies were used as an undiluted culture supernatant.

Hybridomas found to produce the desired monoclonal antibodies were cloned twice by limiting dilution and propagated in culture or in mice. Using this procedure, hybridomas designated HH14 and HH11 were obtained. These hybridomas haveen been deposited at the American Type Culture Collection under ATCC Nos. HB9299 and HB9298, respectively.

Figure 4A:
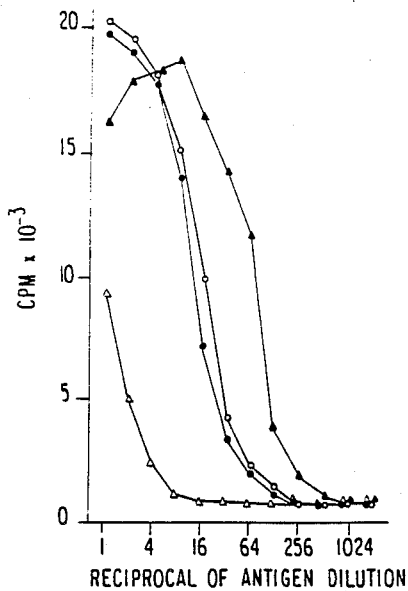
FIG. 4A graphically illustrates the binding specificity of monoclonal antibodies obtained from hydridoma HH11 to various purified glycolipids.
Figure 4B:
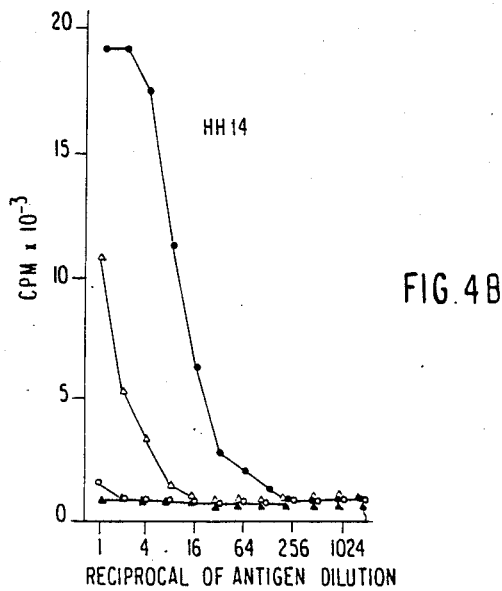
FIG. 4B graphically illustrates the binding specificity of monclonal antibodies obtained from hybridoma HH14 to various purified glycolipids.

Monoclonal antibodies from HH11 and HH14 were then harvested from culture medium or ascites fluid and tested for binding specificity using a solid phase radioimmunoassay as described above. The results are shown in FIGS. 4A and 4B. In FIGS. 4A and 4B, the designations are as follows: Type 3 chain A; A-associated H-antigen; o Type 4 chain A; and Δ Type 4 chain H. FIG. 4A demonstrates that monoclonal antibodies obtained from HH11 were found to react with the A-associated H-antigen, however, binding was also found to the Type 3 chain A, Type 4 chain A and Type 4 chain H antigens. FIG. 4B demonstrates that the monoclonal antibody obtained from HH14 was found to be highly specific for A-associated H-antigens, although weak binding was observed to Type 4 chain H. However, no binding was found to any other H antigens (e.g., Type 1 chain H or Type 2 chain H) or any A antigens e.g., Type 1 chain A, Type 2 chain A, Type 2 chain galactosyl-A, Type 3 chain A or Type 4 chain A) or Fucosyl-GM1 antigens. Therefore, monoclonal antibodies obtained from HH14 are preferred because of their selective binding specificity.

EXAMPLE 4

Blood Typing Assay

Hemagglutination assays were carried out with monoclonal antibodies obtained from HH14 and HH11 as described in Kabat, E. A. et al., *Experimental Immunochemistry*, 2d Ed., Thomas Publishers, Springfield, Ill. (1967) and Clausen, H. et al., *Proc. Natl. Acad. Sci.,* U.S.A., 82:1199–1203 (1985). The results of the assay are set worth in Table III below.

TABLE III

|  | Intact | | | Trypsin treated | | | Sialidase treated | | |
|---|---|---|---|---|---|---|---|---|---|
|  | $A_1$ | $A_2$ | O/B | $A_1$ | $A_2$ | O/B | $A_1$ | $A_2$ | O/B |
| HH11 sup. | 16 | 32 | 0 | 128 | 256 | 0 | 32 | 64 | 0 |
| HH11 asc. | 640 | 640 | <20 | 2560 | 5120 | <20 | 1280 | 640 | <20 |
| HH14 sup. | 0 | 0 | 0 | 0 | 0 | 0 | 0 | 0 | 0 |
| HH14 asc. | <20 | <20 | <20 | <20 | <20 | <20 | <20 | <20 | <20 | in Table III, the numbers indicate reciprocals of the maximum dilution causing observable hemagglutination. For culture supernatant antibody (sup.) antibodies, O indicates that undiluted antibody did not cause agglutination. For asciates (asc) antibodies, the minimum dilution tested was 1:20. Erythrocytes were either tested intact, or after trypsin treatment (0.05% (w/v) at 37° C. for 1 hour) or after sialidase treatment (0.1 unit/ml (Cl. perfringes type X, Sigma, Chemical Co.) at 37° C. for 1 hour) (see Clausen, H. et al, *Proc. Natl. Acad. Sci.,* U.S.A., 82:1199–1203 (1985) for investigating possible masking effects of trypsin or sialidase sensitive structures. Agglutination was read after incubation of antibodies and erythrocytes for 1 hour at 4° C.

As is clear from the results in Table III above, antibodies from HH11, which have specificity for both the A-associated H-antigens and the Type 3 chain A antigens, strongly hemagglutinated $A_1$ and $A_2$ erythrocytes in approximately equal dilutions but not O/B erythrocytes. This is in contrast to Type 3 chain A specific antibodies like TH1 (see Clausen et al., *Proc. Natl. Acad. Sci.,* U.S.A., 82:1199–1203 (1985)). This demonstrates the significance of the A-associated H-antigens for hemagglutination of minor and major blood group A subgroups.

The results in Table III above also demonstrate that monoclonal antibodies obtained from HH14 which have specifity for the A-associated H-antigens, did not agglutinate $A_1$ and $A_2$ erythrocytes. Thus, while HH14 can be used to produce highly specific monoclonal antibodies to the hapten of the A-associated H-antigen, these monoclonal antibodies are not as useful in a hemagglutination assay as those obtained from HH11, although such can be useful in the other blood typing assays described above. It should be noted that the ability of an antibody to agglutinate erythrocytes is not related to the specificity of the antibody but, rather, a poorly understood unrelated characteristic. By including both specificity and agglutination characteristics during selection, it is possible to obtained monoclonal antibodies with both desired characteristics.

While this invention has been described in detail and with reference to specific embodiments thereof, it will be apparent to one skilled in the art that various changes and modifications could be made therein without departing from the spirit and scope thereof.

I claim:

1. A monoclonal antibody having binding specificity for the hapten of the A-associated H-antigen having the following structure:

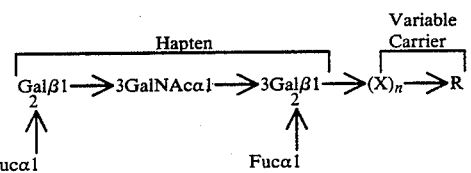

wherein X is a sugar residue and n=0 or a positive integer and wherein R is a primary amino group containing material selected from the group consisting of a polypeptide, a primary amino group containing lipid or a primary amino group containing support.

2. The monoclonal antibody of claim 1, wherein R is a primary amino group containing support.

3. The monoclonal antibody of claim 2, wherein said primary amino group containing support is selected from the group consisting of amino derived silica and amino-derived porous glass beads.

4. The monoclonal antibody of claim 1, wherein R is a polypeptide.

5. The monoclonal antibody of claim 4, wherein said polypeptide is selected from the group consisting of bovine serum albumin, keyhole limpet hemocyanin and egg ovalbumin.

6. The monoclonal antibody of claim 1, wherein R is a primary amino group containing lipid.

7. The monoclonal antibody of claim 6, wherein said primary amino group containing lipid is selected from the group consisting of ceramide, n-octadecylamine and n-hexadecylamine.

8. The monoclonal antibody of claim 1, wherein X is a sugar residue selected from the group consisting of a residue of β-D-galactose, β-D-glucose, β-D-N-acetylglucosamine, β-D-N-acetylgalactosamine, α-L fucose, α-D-galactose, α-D-acetylgalactosamine, α-D-mannose and β-D-mannose.

9. The monoclonal antibody of claim 1, wherein n is 0 to 30.

10. The monoclonal antibody of claim 9, wherein n is 0 to 10.

11. The monoclonal antibody of claim 1, wherein said monoclonal antibody is produced by a hybridoma selected from the group consisting of hybridomas HH11 and HH14 having the identifying characteristics of ATCC Nos. NB 9298 and HB 9299, respectively.

12. The monoclonal antibody of claim 11, wherein said monoclonal antibody is produced by hybridoma HH11 having the identifying characteristics of ATCC No. HB 9298.

13. A hybridoma which produces a monoclonal antibody having binding specificity for the hapten of the A-associated H antigen having the following structure:

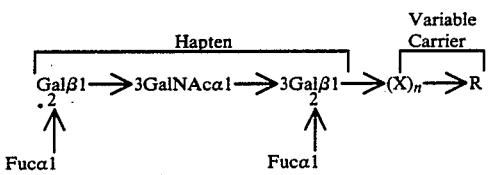

wherein X is a sugar residue and n=0 or a positive integer and wherein R is a primary amino group containing material selected from the group consisting of a polypeptide, a primary amino group containing lipid or a primary amino group containing support.

14. The hybridoma of claim 13, wherein R is a primary amino group containing support.

15. The hybridoma of claim 14, wherein said primary amino group containing support is selected from the group consisting of amino derived silica and amino-derived porous glass beads.

16. The hybridoma of claim 13, wherein R is a polypeptide.

17. The hybridoma of claim 16, wherein said polypeptide is selected from the group consisting of bovine serum albumin, keyhole limpet hemocyanin and egg ovalbumin.

18. The hybridoma of claim 13, wherein R is a primary amino group containing lipid.

19. The hybridoma of claim 18, wherein said primary amino group containing lipid is selected from the group consisting of ceramide, n-octadecylamine and n-hexadecylamine.

20. The hybridoma of claim 13, wherein X is a sugar residue selected from the group consisting of a residue of β-D-galactose, β-D-glucose, β-D-N-acetylglucosamine, β-D-N-acetylgalactosamine, α-L fucose, α-D-galactose, α-D-acetylgalactosamine, α-D-mannose and β-D-mannose.

21. The hybridoma of claim 13, wherein n is 0 to 30.

22. The hybridoma of claim 21, wherein n is 0 to 10.

23. The hybridoma as claimed in claim 13, wherein said hybridoma is selected from the group consisting of HH11 and HH14 having the identifying characteristics of ATCC Nos. HB 9298 and HB 9299, respectively.

24. The hybridoma as claimed in claim 23, wherein said hybridoma is HH11 having the identifying characteristics of ATCC No. HB 9298.

* * * * *